United States Patent [19]
Stevenson

[11] Patent Number: 6,136,313
[45] Date of Patent: Oct. 24, 2000

[54] PROCESSES AND INTERMEDIATES FOR SYNTHETIC ANTIBODY DERIVATIVES

[75] Inventor: George T. Stevenson, Southampton, United Kingdom

[73] Assignee: Imperial College Innovations Limited, London, United Kingdom

[21] Appl. No.: 08/403,520

[22] Filed: Mar. 13, 1995

Related U.S. Application Data

[63] Continuation-in-part of application No. 07/949,492, filed as application No. PCT/GB91/00633, Oct. 23, 1992, abandoned.

[30] Foreign Application Priority Data

Apr. 23, 1990 [GB] United Kingdom ............ 9009106

[51] Int. Cl.[7] .............. A61K 39/395; C07K 16/00; C07K 17/00
[52] U.S. Cl. ................. 424/178.1; 424/134.1; 424/179.1; 424/809; 530/387.1; 530/387.3; 530/391.1; 530/391.9
[58] Field of Search ............. 424/134.1, 178.1, 424/179.1, 809; 530/391.1, 391.9, 387.1, 387.3

[56] References Cited

U.S. PATENT DOCUMENTS 4,719,107  1/1988  Carosella .

FOREIGN PATENT DOCUMENTS

| | | |
|---|---|---|
| 0376770 | 7/1990 | European Pat. Off. . |
| 3444765 | 6/1985 | Germany . |
| WO 9004413 | 5/1990 | WIPO . |

OTHER PUBLICATIONS

Stevenson, G.T., et al., Chemical Abstracts, vol. 110, No. 23, Abstract No. 110:210562a, pp. 552–553, (1989).
Stevenson, et al., Molecular and Cellular Biochemistry, vol. 91:33–38, (1989).
Stevenson, et al., Anti–Cancer Drug Design, vol. 3:219–230; (1989).
Waldmann, T.A., et al., Science, vol. 252, pp. 1657–1662 (1991).
Hawkins, Robert E., et al., BMJ, vol. 305, pp. 1348–1352, (1992).
Rudinger, J., Peptide Hormones, Parsons (edited), University Park Press, pp. 1–7 (1976).
Stevenson et al. (1985a) Cancer Surveys 4(1):213–244.
Watts et al., (1985) Mol. Immunol. 22(7):803–810.

*Primary Examiner*—Ponnathapura Achutamurthy
*Attorney, Agent, or Firm*—Nixon & Vanderhye

[57] ABSTRACT

This invention is directed to intermediates for use in the preparation of chimeric antibodies and synthetic antibody derivatives. The intermediates are open- or closed-hinge Fc fragments that have at least one alkylated external sulphydryl group. The invention is also directed to processes for making such intermediates, chimeric antibodies or synthetic antibody derivatives produced from the intermediates, and to methods of treating B-cell Lymphoma by administering chimeric antibodies or synthetic antibody derivatives produced using the intermediates of the invention.

36 Claims, 5 Drawing Sheets

PROCESSES AND INTERMEDIATES FOR SYNTHETIC ANTIBODY DERIVATIVES

CROSS-REFERENCE TO RELATED APPLICATIONS

This application is a continuation-in-part application of U.S. patent application Ser. No. 07/949,492, filed Oct. 23, 1992, now abandoned which is the U.S. national stage entry of PCT Application No. PCT/GB91/00633, filed Apr. 22, 1991 which claims priority to application GB9009106.7, filed Apr. 23, 1990.

Co-pending application PCT/GB89/01269 (published as WO 90/04413) relates to antibody derivatives having two or more Fc fragments and to processes and intermediates for making such derivatives.

Both the parent application, Ser. No. 07/949,492, and this continuation-in-part application relate to alternative intermediates and processes for making the intermediates which have advantages in certain respects over those described in the earlier co-pending application PCT/GB89/01269.

FIELD OF THE INVENTION

This invention is in the field of antibodies, specifically directed to antibody intermediates which are Fc fragments having a controlled number of chemically functional groups. The Fc antibody intermediates of this invention can be used to build chimeric antibodies and synthetic antibody derivatives that exhibit Fc regions.

BACKGROUND OF THE INVENTION

Antibody derivatives with multiple Fc fragments have a variety of therapeutic applications, especially when the Fc fragments are linked to Fab fragments or functionally similar moieties to form combinations having "chimeric" properties. When chimeric antibodies are used as immunotherapeutic agents, the Fc fragments used to make the intermediates should be derived from the same species as the intended recipient to minimize antigenicity and maximize recruitment of natural effectors. Thus, human Fc fragments are preferred for making chimeric antibodies that are intended for use as immunotherapeutic agents in humans.

Chimeric antibodies in which the Fc fragments are derived from normal human IgG and the Fab fragments are derived from xenogeneic antibody (usually mouse monoclonal IgG) maximize cytotoxicity mediated via recruitment of natural effectors. The preparation of chimeric antibodies in which the antigen binding (Fab) arms of rodent IgG antibody are chemically linked by thioether bonds to human IgG, or to the Fc-gamma portion of human IgG, has been reported in Stevenson et al., "Surface Immunoglobulin of B-lymphocytic Tumours as a Therapeutic Target," Cancer Surveys, 4:213 (1985). A chemically synthesized FabFc chimera was prepared in quantity from monoclonal anti-Id and used in the treatment of human lymphoma as described in Hamblin et al., Blood, 42:495 (1987).

This chemically-derived FabFc chimera exhibited the advantages expected from displaying human instead of rodent Fc-gamma of better recruitment of effectors (complement and various cells displaying Fc-gamma receptors), a longer metabolic survival and a lower immunogenicity. A comprehensive review of work in this field is contained in Cancer Surveys, Vol. 4 No. 1 (1985) (Stevenson and Glennie).

It has been reported that cooperative binding between Fc-gamma and the host's natural effector molecules are enhanced by having two Fc-gamma fragments on each synthetic antibody molecule. Synthetic antibodies having multiple Fc fragments have been constructed by chemically joining two synthetic chimeric antibodies, each having a mouse Fab-gamma fragment linked via a thioether bond [—S—R—S—] to a human Fc-gamma fragment. The two chimeric antibodies are joined via a thioether bond between their two respective Fc-gamma fragments to form bisFab—Fc [FabFc—S—R—S—FcFab]. Stevenson, et al., "A Chimeric Antibody with Dual Fc Regions (bisFabFc) Prepared by Manipulations at the IgG Hinge," Anti-Cancer Drug Design, 3:219–230 (1989) and Stevenson, "Attack on Neoplastic Cell Membranes by Therapeutic Antibody," Molecular and Cellular Biochemistry, 91:33–38 (1989).

SUMMARY OF THE INVENTION

The construction of chimeric antibodies or synthetic antibody derivatives has advantageously been improved with the design of the Fc antibody intermediates of this invention. The Fc intermediates are Fc fragments, having a controlled number of chemically functional groups which may be reacted with complementary functional groups on other moieties. The Fc antibody intermediates are suitable for use in constructing chimeric antibodies or synthetic antibody derivatives of a variety of combinations, including having multiple Fc fragments, in a controlled, predictable and efficient manner. Further, the intermediates of the present invention provide Fc fragments which can be stored for long periods of time, making them convenient to use.

Thus, the present invention provides intermediates for making synthetic chimeric antibodies or synthetic antibody derivatives, including having multiple Fc fragments, processes for making the intermediates, and chimeric antibodies or synthetic antibody derivatives made from the intermediates. These antibody products can then be applied in therapeutic indications, where, upon delivery of the Fc-containing chimeric antibody or synthetic antibody derivative, natural effectors are recruited by antibody Fc in order to destroy antibody-coated cells.

DESCRIPTION OF THE DRAWINGS

FIG. 5 illustrates an Fc fragment in which one external SH group forms a disulphide bond to the pyridyl, —SS—Py. The hatched lines indicate a set of noncovalent bonds holding two peptide chairs together. The arrow indicates that there is almost an immediate reconstitution of an interchain SS bond by SS-interchange as the contralateral SH group attacks the new S—S—Py bond (FIG. 5(a)).

DETAILED DESCRIPTION OF THE INVENTION

Fc Antibody Intermediates.

The Fc antibody intermediates of the present invention have the following general formula:

Fc—S—S—X where

S—S is a disulphide bond;

X is a group which is protonated at a relatively low pH of about 5 or less, more preferably at a pH of between about 3 to about 5, and even more preferably at a pH of about 4 to about 4.5, such that said disulfide bond to X, S—S—X, is electrophilic and susceptible to reduction at a pH of about 5 or less, at which pH other disulphide bonds are resistant to reduction; and Fc is an Fc fragment, comprising four external sulphydryl groups, wherein said sulphydryl group on said Fc that is incorporated into said disulphide bond to X, S—S—X, is electrophilic and susceptible to reduction at a relatively low pH of about 5 or less, at which pH the three remaining external sulphydryl groups on said Fc are inert due to alkylation or in-corporation into an interchain disulphide bond.

The symbol "SS" will henceforth be used to designate a disulphide bond.

By the term "external" sulphydryl groups is meant those sulphydryl groups released by reduction of interchain disulphide bonds. These external sulphydryl groups are distinguished from sulphydryl groups arising from reduction of intrachain disulphide bonds. Intrachain bonds are buried internally in the protein and are difficult to reduce without substantially unfolding the protein; therefore, they remain intact throughout all manipulations referred to in this application. Sulphydryl groups are hereinafter referred to as "SH groups." It will be understood by those skilled in the art that "inert" is not an absolute term. In this context, it is intended to mean stable under process conditions to which the intermediate is to be subjected and in conditions of use, thus distinguishing inert from temporary masking groups, such as sacrificial groups, and the like.

Incorporation of an external sulphydryl group into a disulphide bond to X renders the disulphide bond unusually electrophilic and susceptible to reduction at relatively low pH values of about 5 or less, typically between about 3 to about 5. However, the disulphide bond to X, S—S—X, is sufficiently inert to permit storage of the intermediate Fc—SS—X over a pH range of about 5 to about 8.

The group "X" is a group that is protonated at a relatively low pH, preferably at a relatively low pH of about 5 or less, more preferably at a relatively low pH of between about 3 to about 5, and even more preferably at a pH of about 4 to about 4.5, but that is not protonated at neutral pH. For the purpose of this invention, a protonated group is defined as a group that causes the disulphide linkage in which it is involved to become electrophilic and susceptible to reduction (i.e. highly electrophilic) at a relatively low pH. As the pH is lowered from neutral pH to a pH of about 3 to about 5, the group X acquires a positive charge due to protonation; the positive charge renders the adjacent SS disulphide bond electrophilic. The range of effective pH is about 5 or less, preferably between about 3 to about 5, with pH about 4 to about 4.5 being more preferred. Protein disulphide bonds, such as intrachain and interchain disulphide bonds, are not electrophilic in the pH range of about 3 to about 5; in this pH range they are highly resistant to reduction.

The group "X" can thus be any group which contains a primary amino group close to a disulphide bond because these groups will be protonated at a relatively low pH. Two examples of primary amino groups close to a disulphide bond that are protonated at a relatively low pH are dithioethylamine and dithio-phenylamine.

Figure 1A:
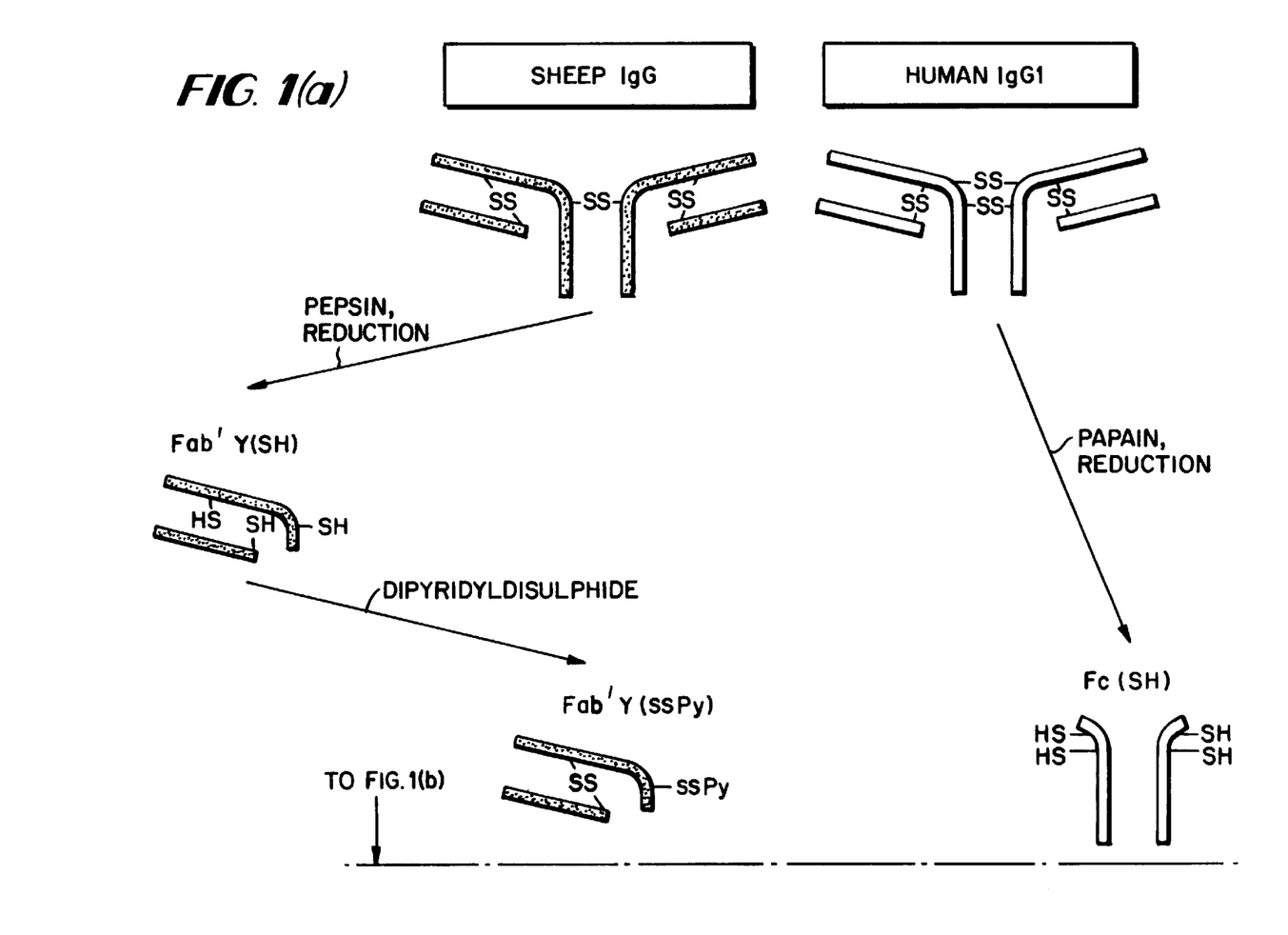
FIG. 1 illustrates the preparation of a precursor to the intermediate of the invention, of the form Fab—SS—Fc, in which a sacrificial Fab is combined with an Fc fragment having a sulphydryl group which has been rendered inert by alkylation (represented in the drawings by the symbol So).
Figure 1B:
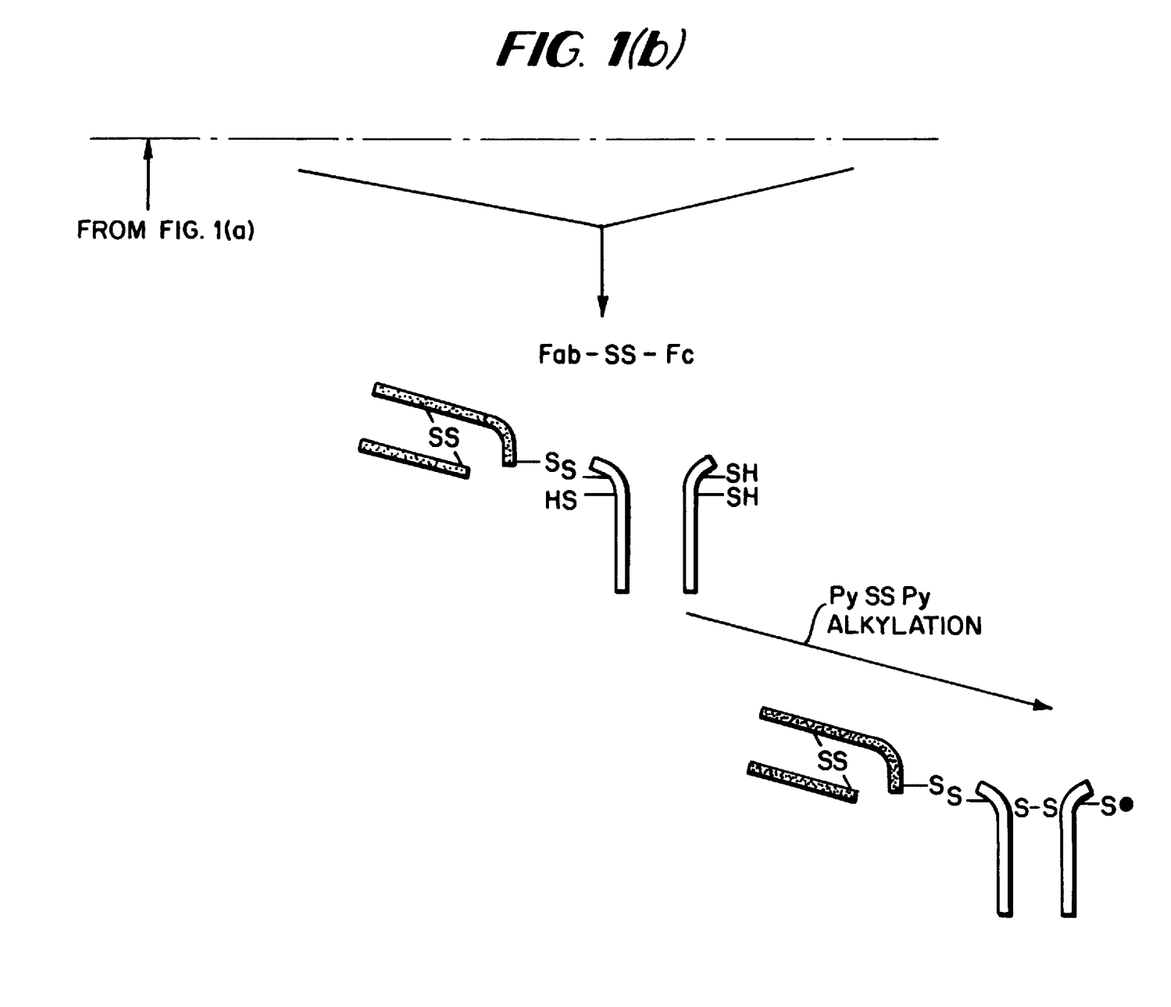

The group X is preferably pyridyl derived from pyridyl-containing disulphides in which a disulphide bond is attached to the pyridyl ring at position 2 or 4. Pyridyl is not a protonated group at a near-neutral pH. However, as the pH is lowered, the SS bonds in pyridyl disulphide (e.g. 2,2'-dipyridyl disulphide and 4,4'-dipyridyl disulphide) become highly electrophilic and susceptible to reduction as the pyridyl nitrogen atoms begin to be protonated. The pKs for protonation of the first ring nitrogen are approximately 2.3 (for the 2,2' derivative) and 5.0 (for the 4,4' derivative), but high reactivities are apparent even at pH 6 as shown in FIG. 1 of Grimshaw et al, J. Am. Chem. Soc., 101:1521–1532 (1979). The conveniently flat curves for pH versus reaction rate shown in FIG. 1 of Grimshaw et al. reflect the fact that as the pH is lowered further, the pyridyl disulphides become more electrophilic; but the thiol with which they are reacting (mercaptoethanol in the case of FIG. 1 of Grimshaw et al.) becomes less reactive as it itself is progressively protonated. At a pH of about 3 to about 5 the protein—SS—Py linkage is unusually electrophilic and is therefore readily reduced by such agents as dithiothreitol; however, other non-protonated disulphide bonds are stable and resistant to reduction at a pH of about 3 to about 5. The advantages arising from pyridyl disulphide (symmetrical or mixed) being able to react with thiols such as Fab and Fc fragments at relatively acid pHs are explained and set out in Brocklchurst, Int. J. Biochem., 10:259–274 (1979).

The term "Fc antibody fragment" is intended to include not only, for example, typical immunoglobulin Fc structures comprising two peptide chains, but also fragments of Fc which retain Fc activity, e.g. recruitment effector ability or involvement in Ig transport and metabolism. Fc fragments may be derived from immunoglobulin of any immunoglobulin class or animal species. If intended for human use, however, Fc fragments are preferably derived from human immunoglobulin, e.g. IgG or IgG1 (a subclass of IgG). Fc fragments may be selectively derived from the patient who is ultimately destined to be treated with chimeric antibodies made from the claimed intermediates. Polyclonal or monoclonal sources of Fc fragments may be used.

Procedures for Preparation.

In general terms, intermediates of the present invention may be produced by the following process steps:

a. combining an Fc fragment with a temporary "sacrificial" group;

b. subjecting the combination so formed to disulphide interchange and rendering potential reactive (SH groups) inert either by incorporation into an interchain disulphide bond or by alkylation;

c. separating the sacrificial group from the Fc fragment to leave a solitary reactive site (SH group) on the Fc fragment; and d. attaching a protonated group X to the reactive SH group via a disulphide bond thereby rendering the disulphide bond electrophilic and susceptible to reduction at a pH of about 3 to about 5. This SH group is temporarily inert.

The sacrificial group must be selected to have sufficient molecular weight to enable separation of the sacrificial group-Fc conjugate, shown in FIG. 1 as Fab—SS—Fc, from other reaction products by chromatographic fractionation or the like. Generally, sufficient molecular weight for a sacrificial group according to the invention is a molecular weight greater than or equal to that of the Fc fragment to which it is bound. When a sacrificial group having a molecular weight at least as great as that of the Fc fragment, the conjugate can be readily separated from nonconjugated Fc fragments by, for instance, gel chromatography.

The sacrificial group must itself be capable of forming a temporary bond with a protonated group X, such that the —SS—X bond is electrophilic and thus susceptible to reduction at a pH of between about 3 to about 5. The sacrificial group substituted with —S—S—X is then conjugated with the reactive SH group on the Fc fragment.

One such suitable sacrificial group, for example, is an Fab fragment from sheep immunoglobulin. Sheep immunoglobulin is a cheap and readily available source of providing an $Fab_2$ fragment having a single inter-gamma disulphide bond. The inter-gamma disulphide bond in the $Fab_2$ fragment can be cleaved to yield Fab with a solitary external SH group (Fab—SH) that can be derivatized to Fab—SS—X. Another suitable group is human serum albumin.

The procedures of this invention will be further illustrated with the following description of two basic processes: one process produces a closed-hinge intermediate and the other process produces an open-hinged intermediate.

Preparation of A Closed-Hinge Intermediate, Fc—SS—Py.

The preparation of a closed-hinge intermediate is described, using as an illustration, the closed-hinge intermediate Fc-gamma-dithiopyridine (pyridyl-Fc, Fc—SS—Py), a stable derivative of a human normal IgGl with a single pyridyl group protruding from a cysteine residue in the Fc-gamma hinge. When required for use Fc—SS—Py is quickly converted to its active form Fc-gama-monomaleimide (Fc-mal), in which the hinge cysteine bears a metastable maleimidyl group. This group enables the Fc-gamma to be linked to any protein with an accessible SH group, yielding chimeric derivatives joined by thioether bonds.

The preparation of dosed-hinge Fc-gamma-dithiopyridine intermediate, Fc—SS—Py, begins with papain digestion of human normal IgG1 to yield Fc-gamma. An initial reduction of the Fc-gamma hinge releases four SH groups from the two parallel inter-gamma SS bonds. One of these SH groups is protected by temporary incorporation into an SS link to a disposable protein (sacrificial group) (human albumin or sheep Fab-gamma). (See FIG. 1 wherein the sacrificial group is Fab-gamma). The remaining three SH groups on the Fc-gamma fragment then undergo a first disulphide interchange with 4,4'-dipyridyl disulphide (Py—SS—Py), reconstituting an inter-gamma SS from the paired SH groups and forming the mixed disulphide Fc—SS—Py from the unpaired SH.

This mixed disulphide Fc—SS—Py is now exposed to dithiothreitol at a relatively low pH, preferably at a pH of about 3 to about 5, more preferably a pH of about 4.0, where the inter-gamma and Fc-gamma-albumin (or Fc-gamma-Fab-gamma) SS bonds are not susceptible to reduction, but the bond in Fc—SS—Py, which is highly electrophilic because of protonation of the pyridyl N, is reduced. A solitary hinge SH results, and is then permanently blocked by alkylation with N-ethylmaleimide (NEM).

Figure 3:
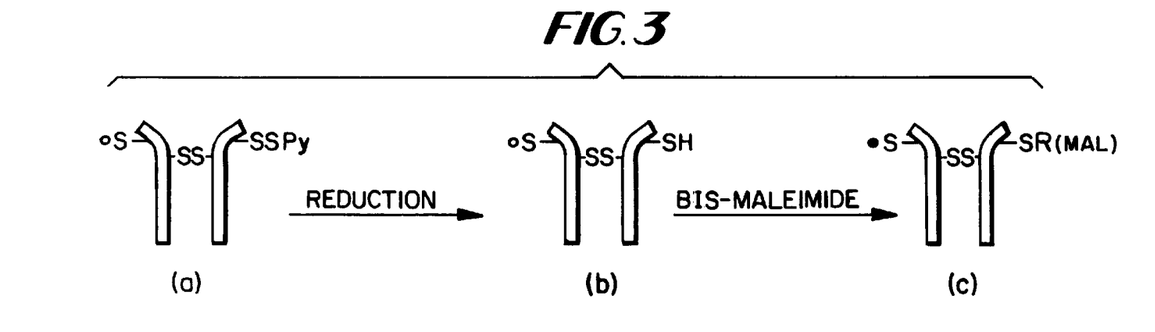
FIG. 3 illustrates an intermediate (a) as provided by the invention and further process steps by which it may be reduced with a dithiol to form (b) followed by reaction with bis maleimide to give a form (c) for further reaction with another moiety.

The Fc-gamma-albumin chimera product is purified chromatographically, cleaved by reduction of all interchain SS, and the albumin is discarded. The Fc-gamma with three hinge SH now undergoes a second round of disulphide interchange with Py—SS—Py to form the final Fc—SS—Py product, with a reconstituted hinge SS and a mixed disulphide (Fc—SS—Py) formed from the unpaired SH. See FIG. 3(a), the closed-hinge form of the intermediate.

When required for use Fc—SS—Py is reduced with dithiothreitol at pH of about 3 to about 5, preferably at a pH of about 4.0, to leave a solitary protein SH which, upon reaction with a molar surplus of a bismaleimide $R-(mal)_2$, forms Fc-gamma —S-succinimidyl-R-maleimide, i.e. Fc-mal.

Preparation of an Open-hinge Intermediate.

The preparation of the open-hinge intermediate follows the steps of the preparation of the closed-hinge intermediate, but omits the first round of disulphide interchange with Py—SS—Py, and proceeds instead to alkylate all three hinge SH groups after formation of the Fc-gamma-albumin chimera. FIG. 1 shows Fab—SS—Fc, wherein the sacrificial group is Fab.

The open-hinge intermediate is useful when a final open-hinge chimeric antibody or antibody derivative is desired. While open-hinge antibodies lose the ability to activate the classical complement pathway, possibly due to impeded access of Clq heads to splayed C-gamma2 domains, they retain their ability to involve natural killer cell-RIII receptor. The final Fc—SS—Py product then has an open-hinge, which is advantageous in certain situations. For example, therapeutic situations exist where differential loss of complement activation might be desirable, as when free antigen in the blood stream could lead to a dangerous degree of activation.

Uses of Fc—SS—X.

The intermediates of this invention may be stored and used, when required, to attach human Fc fragments to any agent with a free SH group. The agent conjugated to the intermediate may be selected to target undesirable or abnormal tissue, such as cancer or virus-infected cells, and thereby coat the tissue with Fc in a manner which will attract the destructive power of the host's natural effectors (complement, macrophages, NK cells) with affinities for the Fc. In this situation, the agent would preferably recognize and bind to cell surface molecules on the targeted cells.

Examples of agents suitable for coupling to human Fc include the following:

(1) The Fab-gamma fragment from a monoclonal antibody. Most antibodies readily yield this fragment upon peptic digestion. The chimeric antibody products so produced may be used for:

a. Killing cancer cells in the body, for example in tumors, blood, lymphatic fluid or in bone marrow.
  b. Suppressing host T lymphocytes in graft recipients.
  c. Suppressing graft T lymphocytes in graft-vs-host disease.
  d. Killing virus-infected cells.
  e. Killing auto-immune lymphocytes (with antibody specific for the surface idiotypes, as for a class-specified antigen).

(2) Any other ligand that targets the surface of an undesirable or abnormal cell, such as cancer or virus-infected cells cell, e.g. CD4, which will attach to the viral protein gp120 displayed on the surfaces of HIV-infected cells. This ligand must be able to display an SH group, which may need to be introduced by genetic or chemical engineering.

(3) Lectins which specifically recognize carbohydrate moieties on the targeted undesirable or abnormal cell may be used if the lectin has an available SH group, or is manipulated to have an available SH group.

The intermediates of this invention can also be used to produce and engineer antibody derivatives having improved Fc activity, for example in regard to effector recruitment and a longer half-life. This can be accomplished in the case of immunotherapeutic agents, by using intermediates with Fc fragments derived from the same species as the intended recipient. The intended recipient can be human or animal in the case of veterinary medicines. These chemically engineered antibody derivatives have utility in the treatment of a range of conditions requiring the killing of mammalian cells for example in human cancer therapy, or in other conditions where enhancements of Fc function is beneficial.

Figure 4:
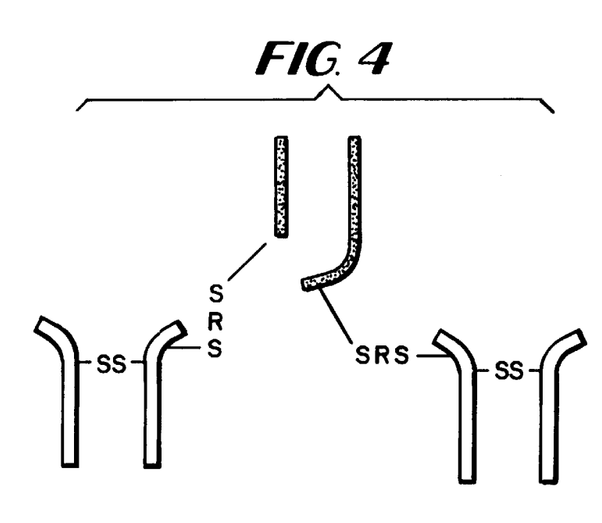
FIG. 4 shows an FabFc$_2$ product of a type which may be constructed from the form illustrated in FIG. 3(c).

The synthetic antibody derivatives made from the intermediates of the invention will usually have at least one Fab fragment but the inventive concept is not limited in this way. Multiple. Fc fragments may, for example, be useful per se as starting material for the construction of more complex structures. Chimeric antibodies having the formula FabFc$_2$, made from intermediates of this invention, comprise two Fc fragments derived from human Immunoglobulin G (IgG) as can be seen in FIG. 4. These chimeric antibodies were tested for their usefulness as immunotherapeutic agents for the treatment of lymphoma in humans and found to be effective at suppressing tumor growth as described in the clinical trial results set forth in Example 7.

It is believed that FabFc$_2$ chimeric antibodies have heightened effectiveness, in part, because doubling of the number of Fc fragments associated with each Fab fragment offers co-operative binding of natural effectors. Other ligands, such as lectins, conjugated to the intermediates of the present invention in the form ligand-multiple Fc, would also display enhanced binding of natural effectors.

Fab fragments for use in synthetic chimeric antibodies or derivatives may be made from any immunoglobulin which provides the desired specificity for targeted undesirable or abnormal cells. Fab regions are preferably derived from monoclonal antibodies, although suitable polyclonals may also be used.

The invention makes possible the production of a range of intermediate and final product structures and a variety of process steps and combinations. Embodiments in addition to those illustrated will be readily understood by those skilled in the art. The present invention includes within its scope novel processes, intermediates and products derived from the invention whether as individual features or in combination with each other or further features to produce novel combinations.

The invention is illustrated further by the following examples, which are not to be taken as limiting in any way.

EXAMPLES

Principles of Preparation of Fc-dithiopyridine (FC—SS—Py).

1. Human normal Fc-gamma (See FIG. 1, top right "HUMAN IgG1"), from the predominant IgG subclass IgG1, is digested in papain to remove the Fab fragments and reduced so that its two interchain hinge SS bonds yield four external SH groups. (See FIG. 1, Fc(SH)$_4$).

2. One of the Fc-gamma SH groups is used to form an SS bond with the disposable sacrificial group, sheep Fab-gamma (See FIG. 1 top, left), yielding the temporary species Fab—SS—Fc. Of the three remaining Fc-gamma SH groups, two are now directed by a first SS interchange to reform one of the original hinge SS bonds. One unpaired SH group, directly opposite that utilized in the SS link to Fab, is blocked permanently by alkylation (See FIG. 1, bottom right.) Other possible reactions which may be used for blocking are discussed by Cecil and McPhee, Advances in Protein Chemistry, 14:255 (1959).

3. Fab—SS—Fc is separated, by gel chromatography, from other products and surplus reagents in the (Fab+Fc) reaction mixture.

Figure 2:
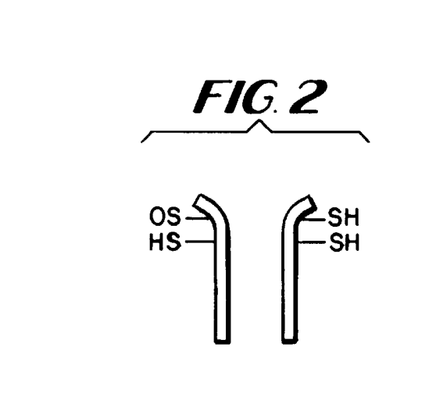
FIG. 2 illustrates a subsequent stage in which the Fc fragment has been separated from the sacrificial Fab.

4. All interchain SS bonds in the Fab—SS—Fc are reduced to yield the structure of FIG. 2 (Fc—(SH)$_3$). The released Fab-gamma is discarded—having served its purpose of permitting the separation of Fc in which one of the original four hinge SH groups has been blocked by alkylation.

5. A second round of SS interchange again reforms the available hinge SS, while the solitary unpaired hinge SH is used to form a dithio(4-)pyridine group (See FIG. 3(a).) This is a closed-hinge form of the intermediate Fc—SS—Py of the present invention.

6. The Fc—SS—Py is stored in this form. When required for use the SS—Py bond can be cleaved by gentle reduction at pH of between about 3 to about 5, preferably at a pH of about 4.0 to about 4.5, and a free maleimide group (R) introduced by reaction with a large molar surplus of bismaleimide linker (e.g. o-phenylenedimaleimide), (see FIGS. 3(b) and 3(c)). Reduction at a pH of about 3 to about 5 does not cleave the hinge SS. The susceptibility to reduction at acid pH shown by —SS—Py can be achieved using as protonated group X, either 2-pyridyl or 4-pyridyl derivatives (the latter being the more susceptible), and is due to increased electrophilicity of the bond as the pyridyl N becomes protonated at the low pH (see Brockelhurst, Int. J. Biochem, 10:259 (1979)).

Principles of Rapid Synthesis of Fc—SS—X.

The rapid synthesis of Fc—SS—X can be used for synthesizing both the open and closed-hinge forms of the intermediate, Fc—SS—X. In this process, reduced Fc fragment having four external sulphydryl groups is treated with an alkylating agent such that either one or three of the sulphydryl groups become alkylated. Where the closed-hinge form is desired, one SH group is alkylated; where the open hinge form is desired, three SH groups are alkylated.

After the appropriate alkylation step, a round of disulphide interchange is conducted which results in the formation of the intermediate Fc—S—S—X due to: (1) reconstitution of original interchain SS bonds wherever paired SH groups corresponding to such bonds are available; and (2) formation of the mixed disulphide Fc—SS—Py wherever unpaired SH groups occur.

Example 6 sets forth the details of preparing both open- and close-hinged Fc—SS—X intermediates using the rapid synthesis method.

Figure 5A:
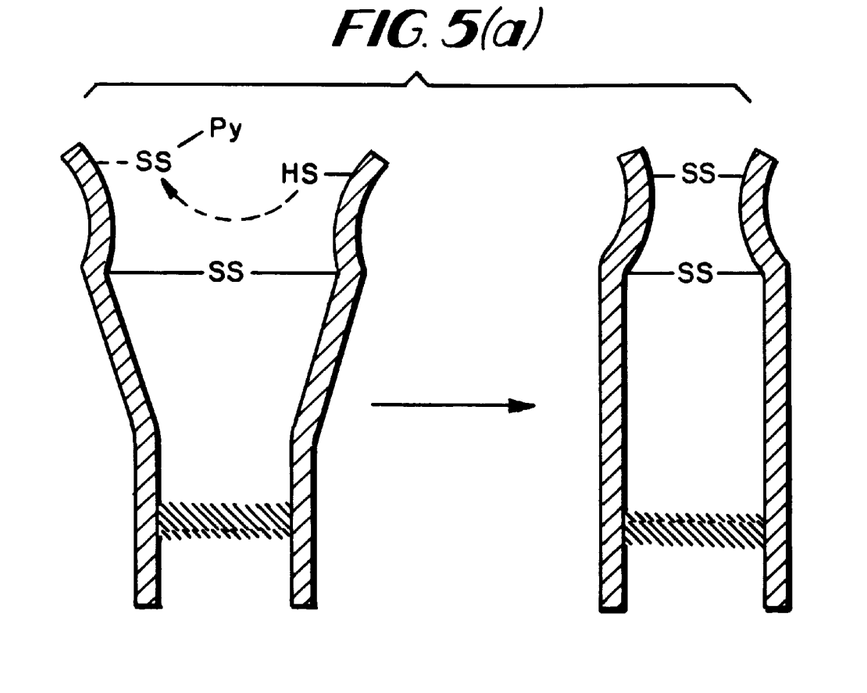

If the disulphide interchange is conducted with Fc(SH)$_4$ without prior alkylation, there is an almost immediate reconstitution of an original interchain SS bond by SS-interchange as the contralateral SH group attacks the new bond (FIG. 5(a)). In order for the new SS—Py bond to survive, the contralateral SH group must be blocked before the first round of disulphide interchange. This is accomplished by alkylating the contralateral SH group. Alkylation of an average of one SH group per Fc (by a reagent such as iodoacetamide or N-ethylmaleimide) is a stochastic process and so leads to the following distribution of alkylated molecules (based on binomial terms):

| Alkylated SH per Fc molecule | Proportion of Fc molecules |
| --- | --- |
| 0 | 0.316 |
| 1 | 0.422 |
| 2 | 0.211 |
| 3 | 0.047 |
| 4 | 0.004 |

It is difficult to fractionate this mixture. The molecules with no SH alkylated pose no problem: at a later stage both their interchain SS will have been reconstituted by SS-interchange, and what is essentially a reconstituted normal Fc-gamma fragment will act simply as inert carrier during subsequent manipulations. However, the molecules with two and three SH alkylated lead to an undesirable concentration of unwanted products.

The problem is eased by alkylating at a lower level (~0.6 SH group per Fc). This leads to a 13% reduction in those molecules alkylated at one site, but it leads to considerably greater reductions in molecules alkylated at multiple sites:

| Alkylated SH per Fc molecule | Proportion of Fc molecules |
| --- | --- |
| 0 | 0.522 |
| 1 | 0.368 |
| 2 | 0.098 |
| 3 | 0.011 |
| 4 | <0.001 |

This distribution of alkylated groups has proved completely acceptable for preparing intermediates of the closed-hinge form.

Proceeding with the preparation of the closed-hinge intermediate, disulphide interchange is now carried out with 4,4'-dipyridyldisulphide, producing the intermediate Fc-dithio-4-pyridine, abbreviated to Fc—SS—Py. The SS—Py bond survives because the contralateral SH group (opposite the SS—Py bond) has been previously alkylated by NEM.

To make the open hinge form of the intermediate, Fc(SH)$_4$ is alkylated at an average of 3.4 sites per molecule. The disulphide interchange will then form the mixed disulphide Fc—S—S—X at the sole remaining external sulphydryl group, the other three remaining SH groups having been alkylated.

Materials.

In the Examples that follow, the following materials were used:

Human albumin, from Sigma Chemical Company.

Human Fc-gamma prepared from human normal IgG, itself obtained from plasma surplus to blood bank requirements, as described by Stevenson et al., Anti-Cancer Drug Design, 3:219 (1989).

Sheep IgG prepared from serum by sequential precipitation with ammonium sulphate and DEAE-cellulose chromatography, and from it sheep F(ab-gamma)$_2$ prepared by a standard peptic digestion (Nisonoff et al, Arch. Biochem. Biophys., 89:230 (1960).

Dithiothreitol (DTT) and N-ethylmalemide (NEM), both from Sigma Chemical Co., used without further purification.

4,4'-dipyridyl disulphide (Py—SS—Py) from Aldrich Chemical Co., was recrystallized from dimethylformamide/water.

SEPHADEX®, a bead-formed gel prepared by cross-linking dextran with epichlorohydrin; SEPHACRYL®, prepared by covalently cross-linking allyl dextran with N,N'-methylene bisacrylamide to give a rigid gel with a carefully controlled range of pore sizes; and Protein A-SEPHAROSE®, a bead-formed gel prepared from agarose, chromatography media available from Pharmacia-LKB, and Phospho-Ultrogel from IBF Biotechnics.

Flow-Chart of Intermediate Preparation.

The preparation of the intermediates of the present invention is summarized in the flow-chart below. In this chart each "+" indicates a chemical reaction, each arrow the loading or unloading of a chromatographic column. The boxed products provide suitable subheadings for the examples that follow.

Example 1

Formation of Fab (S—S—Py)$_1$.

Sheep F(ab-gamma)$_2$ 5mg/ml, obtained by pepsin digestion of sheep IgG, was reduced with 1 mM dithiothreitol (DTT) at pH 8.0, 25° C. for 30 minutes to form three external SH groups. It was then chilled and allowed to undergo SS-interchange at 5° C. for 15 minutes with Py—SS—Py, either 2,2'-dipyridyl disulphide or 4,4'-dipyridyl disulphide, added to 0.5mM surplus to the DTT. During this interchange the Fab-gamma-light interchain SS bond reformed, while the SH derived from the solitary inter-gamma SS emerged as the mixed disulphide Fab—SS—Py. Passage through SEPHADEX® G-25 removed all entities of low m.w. (less than 5000) and transferred the protein to 0.03M acetate, pH 4.5. The protein was then led onto Phospho-Ultrogel A6R equilibrated with the same buffer, and bound to this medium in a compact zone (about 50 mg/cm$^3$). It was finally eluted from the gel at a concentration of about 30 mg/ml with 0.5M NaCl in the same acetate buffer.

Example 2

Formation of Fc(SH)$_4$.

Human Fc-gamma fragments at 20±2 mg/ml, obtained from papain digestion of IgG, were reduced with 3mM dithiothreital (DTT), at pH 8.0, 25° C., for 30 minutes. It was then transferred to 0.1M acetate, pH 4.0, with simultaneous removal of the DTT, by passage through SEPHADEX® G-25. Four external SH groups were formed by reduction of the two interchain disulphide bonds in the hinge region. (See FIG. 1, Fc(SH)$_4$ and the Flow Chart).

Example 3

Formation of Fab—SS—Fc.

The Fab and Fc derivatives from Examples 1 and 2 were mixed and incubated at 25° C. for 30 minutes. During this period the principle reaction occurring was:

Fab(SSPy)$_1$+Fc(SH)$_4$→Fab—SS—Fc+4-thiopyridone. There was also some formation of Fab$_2$Fc and Fab$_3$ Fc. This step is the same for preparation of both the open- and close-hinge forms of the intermediate. At this point, the Fab—SS—Fc precursor has no inter-gamma SS bonds and has three SH groups.

To retain Fab—SS—Fc in the open hinge form, it was alkylated with N-ethylmaleimide to render all three SH groups inert.

To make the closed-hinge form, at the end of the incubation, the mixture containing the Fab—SS—Fc was diluted with 2.8 volumes of cold water and Py—SS—Py, 4,4'-dipyridyl disulphide, was added to 0.17mM. This first disulphide-interchange reconstituted those SS bond in the Fc hinges where both paired cysteine SH remain free, while the unpaired SH emerged as the mixed disulphide, protein-SS—Py. The protein-SS—Py bond was reconverted to protein-SH by treatment with 0.4 mM DTT at pH 4.5. Then all further interchange was halted by alkylating the free SH upon addition of N-ethylmaleimide (NEM) at 2.9 mM. (See FIG. 1, Right).

The protein solution was now concentrated by absorption/desorption on Phospho/Ultrogel, as described for Fab(SSPy)$_1$' and the concentrated solution was led onto SEPHACRYL® S200 equilibrated with 0.5M NaCl, 0.1 M acetate, pH 5.8. The Fab—SS—Fc separated from other proteins and was led onto, and bound to, Protein A-SEPHAROSE® equilibrated with the same buffer.

Example 4

Formation of Fc—SS—Py.

(A) Formation of Fc—SS—Py in the closed-hinge form.

The Fab—SS—Fc product of Example 3 in the closed-hinge form was reduced in DTT, 1 mM at pH 8.0 and led through a Protein-A-SEPHAROSE® column, thereby releasing the Fab-gamma for which the column had no affinity. This step removed the sacrificial group Fab from the Fc-gamma fragment and reduced all disulphide bonds. After washing off the Fab-gamma, the Fc-gamma in the form Fc(SH)$_3$', was eluted with 0.1M glycine HCl, pH 3.0, and immediately transferred into 0.03 M acetate, pH 4.5, by passage through SEPHADEX® G-25.

Finally Py—SS—Py was added to 0.25 mM so that a second SS-interchange again restored the hinge SS and left the remaining non-alkylated unpaired SH group on the cysteine as the mixed pyridyl disulphide (See FIG. 3($a$)). This intermediate was stable upon storage at 5° C. for three months. The stored intermediate was reduced and maleimidated as illustrated in FIG. 3($b$) and ($c$) to give Fc-mal which may be linked to any agent with a SH group, for example, Fab(SH)$_5$ to give FabFc$_2$ as illustrated in FIG. 4.

(B) Formation of Fc—SS—Py in the open-hinge form.

The open-hinge product Fab—SS—Fc of Example 3 was similarly reduced by DTT, 1 mM at pH 8.0 to release the sacrificial group and reformed a solitary SH group at that position. The three SH groups on the open-hinge Fab—SS—Fc have been alkylated. The Fc(SH), open-hinge product was then subjected to a disulphide interchange and formed the open-hinge intermediate Fc—SS—Py with three alkylated SH groups.

Example 5

Preparation of HSA—SS—Fc.

In the above preparation of pyridyl Fc, sheep Fab-gamma was used to form a temporary species Fab—SS—Fc, thereby masking one SH group in the Fc hinge. At the same time, the Fab—SS—Fc has a distinctive molecular weight (about 100,000), which allows it to be separated chromatographically from other reactants. Human serum albumin (HSA) was substituted for sheep Fab-gamma, so as to avoid additional safety precautions which might be required due to the introduction of a sheep protein. HSA has a single cysteine residue which served the masking function, and its molecular weight (64,500) endowed the temporary species (HSA—SS—Fc) with a distinctive molecular weight for chromatographic separation.

Human serum albumin (HSA) for use as a sacrificial group has a single cysteine and hence its single SH group is designated as HSA(SH)$_1$. The overall reactions required for preparation of the HSA—SS—Fc species are as follows:

(1)  HSA(SH)$_1$+Py—SS—Py HSA(SS—Py)$_1$+ thiopyridone (2)  HSA(SS—Py)$_1$+Fc(SH)$_4$HSA—SS—Fc+ thiopyridone Due to the fact that the SH group on HSA is relatively unreactive with other proteins, apparently not being readily accessible on the protein surface (see Cecil & McPhee, Advances in Protein Chemistry, 14:256 (1959)), it has been found necessary to add an extension arm terminating in an SH to the cysteine residue before proceeding with reaction (1). Reactions (1) and (2) can then carried out as described above for sheep Fab-gamma.

The preliminary steps required for HSA were as follows:

(a) HSA (Sigma Chemical Company) was first reduced at pH 7.0 with dithiothreitol (2mM) to ensure that its cysteine residue was fully in the reduced (SH) form. It was then passed through SEPHADEX® G-25 (Pharmacia), equilibrated with 0.02M acetate buffer, pH 5.0 and run at 5° C.

(b) The protein was then reacted with o-phenylenedimaleimide (1.2 mM, pH 5.0, dimethylformamide 16% v/v) at 5° C. for 60 minutes, to yield HSA(mal)$_1$ with an active maleimidyl group, and was again separated from reactants of a molecular weight that are less than 5,000 by passage through SEPHADEX®.

(c) Finally, the protein was reacted again with dithiothreitol (1 mM) to yield HSA(SH)$_1$' with its SH group located at the end of an arm about 15 Å long.

Example 6

Rapid Synthesis of Fc—SS—X.

The steps of papain digestion and reduction to obtain Fc(SH)$_4$ from human normal IgG1 as set forth in Examples 1 and 2 were followed. In order to make the closed-hinge form of the Fc—S—S—X intermediate, Fc(SH)$_4$ was alkylated at an average of 0.6 sites per molecule by addition of N-ethylmaleimide, the reaction being allowed to proceed to completion. To make the open-hinge intermediate, Fc(SH)$_4$ was alkylated at an average of 3.4 sites per molecule.

Disulphide interchange was then carried out with either 2,2'-dipyridyl disulphide or 4,4'-dipyridyl disulphide. This resulted in (1) reconstitution of original interchain SS bonds wherever paired SH groups corresponding to such bonds were available, as depicted in FIG. 5(a); and (2) formation of the mixed disulphide Fc—SS—Py wherever unpaired SH groups occurred, as depicted in FIG. 5(b), where it may be noted that the contralateral SH group, opposite the SS—Py group, was previously alkylated by NEM.

If the Fc(SH)4 was alkylated at an average of 3.4 sites per molecule, there were no paired SH groups and thus the open hinge form of the intermediate resulted.

Figure 5B:
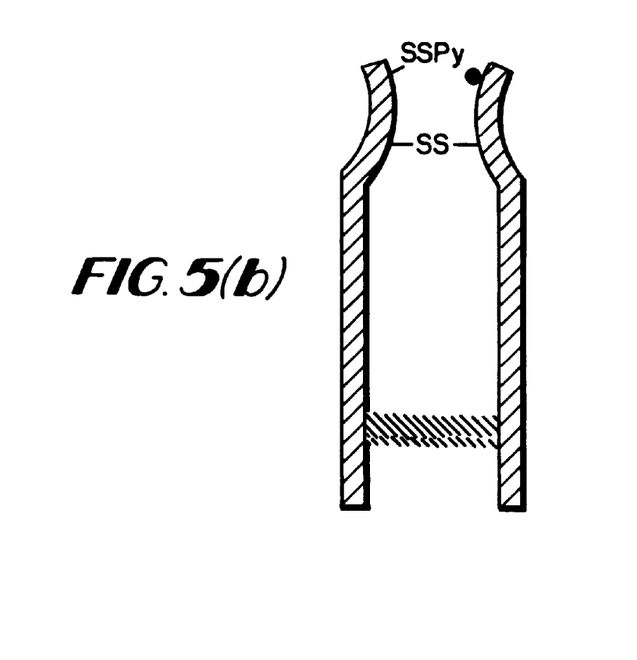
FIG. 5(b) shows that alkylation of the contralateral SH group prior to the first round of disulphide interchange permits the SS—Py bond to survive.

When alkylation was carried out at an average of 0.6 sites per molecule, followed by disulphide interchange to make the closed-hinge intermediate, it is estimated that 52% of the molecules are unchanged Fc-gamma fragments, about 7% (two thirds of those alkylated at two sites) have two —S—S—Py groups, about 1% have one —S—S—Py with no SS at the hinge, and about 37% have the desired configuration shown in FIG. 5(b).

After removal of surplus 4,4' Py—SS—Py, the Fc—SSPy intermediate, in open-or closed-hinge form, was stored without further purification. When required for use, the disulphide bond Fc—S—S—Py was reduced at pH of about 4 with dithiothreitol to leave a solitary protein SH which, upon reaction with a molar surplus of a bismaleimide, formed the metastable Fc—S—R maleimide (Fc-mal).

Example 7

Clinical Trials Using FabFc2 Chimeric Antibodies Made from the Closed-Hinge Intermediates and Comparison with Bispecific Antibodies.

Two preliminary clinical trials of antibody treatment of B-cell lymphoma were conducted. Advanced lymphoma was treated with chimeric FabFc$_2$, in which mouse Fab-gamma was linked to two human Fc-gamma1 fragments so as to recruit natural effectors to tumor targets. Terminal lymphoma was treated with bispecific antibody (BsAb) which recruits the ribosome-inactivating protein saporin. These different mechanisms led to interesting differences in patterns of tumor clearance.

Materials and Methods.

Eight patients were treated with chimeric antibody of two specificities, each at 12 mg/kg: anti-CD37, plus either anti-CD38 or anti-CD19, according to tumor phenotype.

Five patients were treated with preformed immune complexes of saporin and F(ab-gamma)$_2$ BsAb.

All patients were adults who had extensive low-grade B-cell lymphoma, either follicular or lymphocyte type, and who had relapsed after two or more courses of chemotherapy. All had their tumor phenotype, in particular the cell-surface markers, assessed by examination of blood supplemented by one or more other examinations such as nodal biopsy, marrow aspiration and trephining, and cytology of effusions.

The mouse Fab-gamma fragment was obtained from mouse monoclonal antibodies which came from the following sources: anti-CD19 (RFB9), G Janossy (London); anti-CD22 (4KB128), D Mason (Oxford); and anti-CD37 (WR17), K Moore (Southampton). Anti-CD38 (AT13/5) was prepared in house. Anti-CD37 was of isotype IgG2a, the other antibodies all of isotype IgG1.

The univalent chimeric derivative FabFc$_2$, in which the hinge of the Fab-gamma derived from mouse IgG antibody was linked to each hinge of two human Fc-gamma$_1$ by tandem thioether bonds, was prepared by chemical engineering as described in the earlier examples. BsAb of F(ab-gamma)$_2$ type were prepared by thioether-linking the hinge of Fab-gamma from anti-CD22 to the hinge of Fab-gamma from an anti-saporin IgG.

Treatment with FabFc$_2$ employed two antibodies for each patient, anti-CD37 plus either anti-CD38 or anti-CD19 according to tumor phenotype. Each antibody was given as three infusions over 3 weeks, to a total of 12 mg/kg. Each infusion was over a 10–12 hour period, and was slowed further if any reaction occurred.

Treatment with BsAb involved infusion of preformed immune complexes of saporin plus two BsAb, anti-CD22/anti-sap-1, and anti-CD22/anti-sap-5. Mixing occurred in the transfusion bag at least 24 hours before administration. The antibodies were present in equal amounts, with a molar ratio of total antibody to saporin of 3.0. These complexes permitted saporin to be doubly anchored to the tumor cell surface, and have been shown to exert toxicity in vitro at much higher titers than complexes with only a single. BsAb. Progressively increasing doses were given up to a maximum of 10 mg of saporin weekly. Infusions took place over periods up to 2 hours. One patient received a total of 34 mg saporin over a period of 140 days. Antibody levels in plasma were assayed by standard double-determinant immunometric ELISA.

Results.

Toxicity of chimeric antibody tended to manifest shortly after beginning an infusion in those patients with neoplastic cells circulating in the blood. Often there were rigors and fever, and in one case bronchospasm. These problems subsided on slowing the infusion. Two patients experienced arthralgia in the 2 days postinfusion without apparent arthropathy. The infusions were often followed by falls in platelet count that could cause concern if the initial count were less than 50,000/uL. Only one anti-antibody response was detected, an anti-idiotype response to the anti-CD37 antibody WR17.

In all patients, all antigen-positive cells in the blood disappeared rapidly (FIG. 6) and any B symptoms (malaise, sweats, or fever) subsided within a reasonable time. Six of the ten patients treated with chimeric antibody exhibited significant reductions in the size of solid tumor which became apparent 3–4 weeks after beginning treatment and continued slowly thereafter. One patient (9(EV)) had a complete response to immunotherapy using the chimeric antibody and two patients (5(IS) and 10(SS)) had a partial response (50% reduction in summed products of perpendicular diameters) at 2 months. Three patients had a minor response (25–50% decrease).

The reductions in tumor mass occurred quite slowly, as is exemplified in the splenic measurement for the patient (IS) given in Table 1. Patient (IS), who had a T-cell rich B-cell follicular lymphoma, remained in partial remission for 18 months after one course of chimeric antibody treatment before relapsing with axillary lymphadenopathy and recurrent splenomegaly. A second partial course of antibody (anti-CD37 plus anti-CD38 achieved a second similar remission in patient IS, together with remission of a pancytopenia that had hitherto persisted throughout most of the illness.

TABLE 1

| Patients IS, first treatment: | CT measurements of spleen |
|---|---|
| Pre-treatment | 8 × 13 × 19.5 cm |
| 2 weeks post-treatment | 7 × 11 × 14 cm |
| 6 weeks post-treatment | 5 × 10 × 12 cm |
| 5 months post-treatment | 4.3 × 9 × 12 cm |

In four patients, including IS, a half-life was determined for the antibody which persisted in plasma at the end of the course of treatment. Values for the half-life lay between 10 and 14 days, and flow cytometry confirmed the presence of functional antibody at about the level indicated by enzyme-linked immunosorbent assay (ELISA). In three of these four patients, there was obvious residual nodal tumor over the period of the determined half-life.

Toxicity owing to BsAb/saporin was minimal. Three patients experienced local inflammation over the vein used for infusion, and two complained of weakness and myalgia without objective signs or rise in serum creatine kinase. One produced antibodies to both mouse Ig and saporin.

Figure 6:
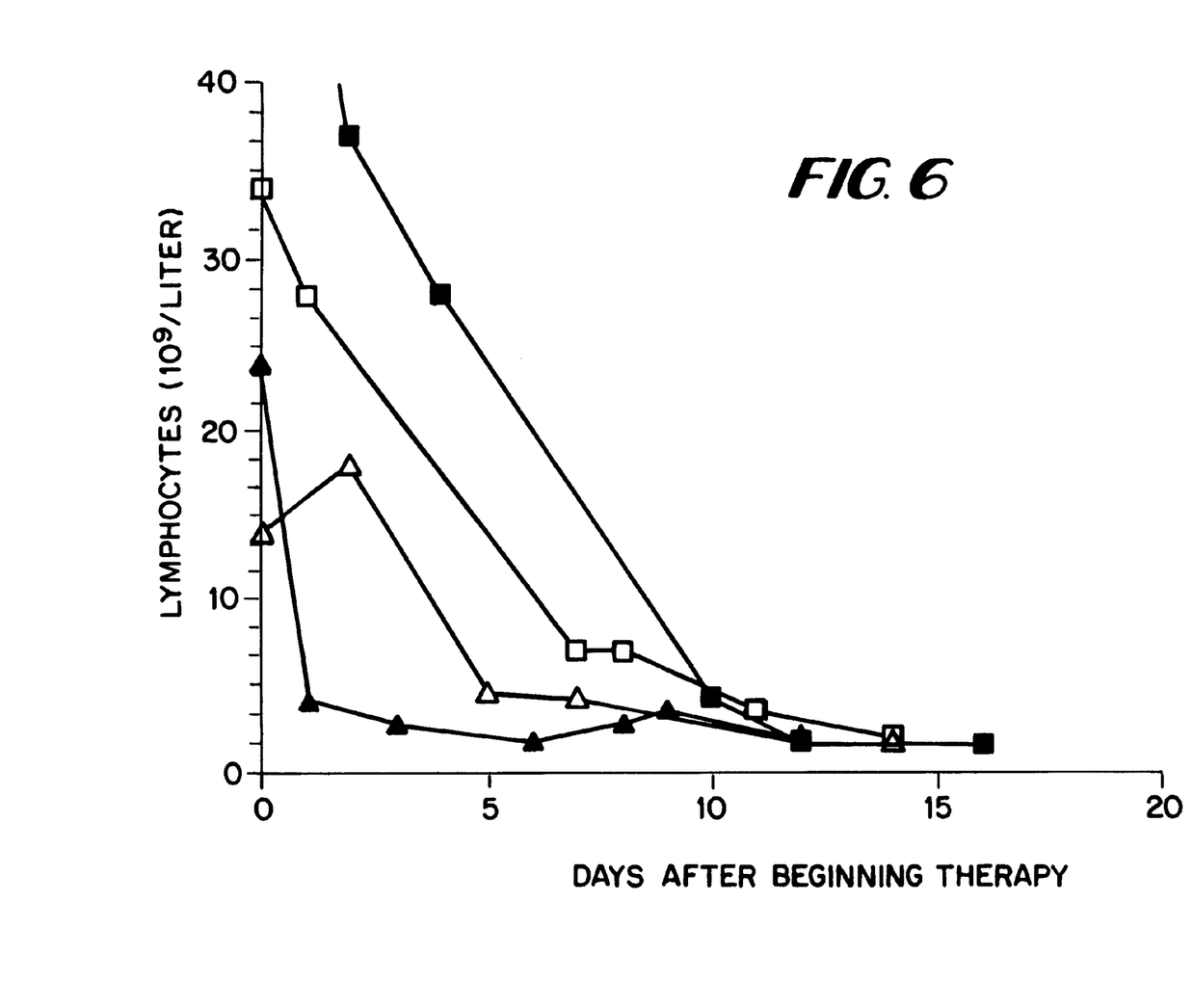
FIG. 6 shows the blood lymphocyte counts in four patients with large numbers of circulating neoplastic B-cells. The antibody treatments remove the B-cells, normal and neoplastic, but spare T- and NK-cells. Two patients received chimeric antibody (solid symbols) and two received BsAb/saporin (open symbols). One patient is seen to have had an initial count lying outside the confines of the graph, at count 72.

All five patients experienced some beneficial response. Where present, tumor cells were cleared from the blood at a somewhat lower tempo than seen with chimeric antibody as shown in FIG. 6. Ascites and pleural effusions were eliminated in the two patients exhibiting them. One patient showed a marked reduction in splenomegaly and two showed a reduction in the size of lymph nodes. Tumor in the marrow appeared to respond well, as there was impressive resolution of pancytopenia when present. However, no patient showed resolution of all tumor, and large nodal masses remained resistant to the doses of BsAb/saporin employed.

The responses of extravascular tumor seen here were more dramatic than occurred with chimeric antibody, and occurred in all patients. Unfortunately, they proved less durable, so that no patient could be said to be in partial remission by conventional criteria at 2 months. Treatment was terminated in one patient because of anti-antibody response, in three because the tumor was no longer responding satisfactorily, and in one because of noncompliance.

Assays of plasma antibody and saporin revealed that the tumor can only have undergone transient exposure to the toxin. F(ab-gamma)$_2$ showed a fractional drop of about two-thirds between 1 and 24 hour postinfusion, and was undetectable (<0.5 ug/mL) at 48 hours, whereas the saporin disappeared with an even steeper slope and was undetectable (<4 ng/mL) at 24 hours.

Discussion.

Reduction of tumor mass by antibodies relying on natural effectors, such as the chimeric FabFc$_2$ antibodies described above, must require both antibody and effectors to permeate the tumor in sufficient amounts.

This clinical trial indicates that immunotherapeutic treatment of B-cell lymphoma with chimeric antibodies made from the claimed intermediates of the present invention, elicited significant reductions in the size of solid tumors in three of the eight patients tested. Chimeric antibodies proved to be advantageous for immunotherapy because they are relatively non-immunogenic due to paucity of foreign determinants and they have a very long half-life which is associated with the possession of a human, host Fc fragment. Chimeric antibodies having a human Fc fragment displayed a vastly longer metabolic survival than is obtained with toxins conjugated to Fab-gamma fragments alone. The results of the clinical trial demonstrated that chimeric antibodies can be safely administered to suppress tumor growth.

The results of the two clinical trials show that when acute destruction of tumor is required, toxin-bearing delivery systems such as the BsAb used here are advantageous. Their efficacy, although limited, is nonetheless impressive when set against the very brief exposure of the tumor cells to saporin. Their major known disadvantages are their toxicity, particularly as exerted on capillary endothelium, and immunogenicity. These factors weigh seriously against their prolonged use for attrition of tumor. By contrast, the chimeric antibody displayed a vastly longer metabolic survival and can probably be relied upon to suppress tumor for a useful period if an initial good remission is achieved.

Example 8

Patients Treated with FabFc$_2$ Antibody.

Table 2 summarizes the clinical trails described in Example 7 and shows the results of two additional patients.

TABLE 2

PATIENTS TREATED WITH FabFc$_2$ ANTIBODY

| Patient | Age | Sex | Diagnosis* | Stage | Neopl. cells in blood (10$^9$/l) | Courses of chemo-therapy | FabFc2 Specif. | Doses | Total mg | Toxicity † | Outcome † |
|---|---|---|---|---|---|---|---|---|---|---|---|
| 1 (IH) | 57 | M | SLL | 4B | 24 | >2 | CD37 | 4 | 400 | 2 | MR$^a$ |
|  |  |  |  |  |  |  | CD22 | 4 | 400 |  |  |
| 2 (AH) | 67 | M | FCL, I | 4A | 0 | >2 | CD37 | 3 | 400 | 1 | Stable |
|  |  |  |  |  |  |  | CD19 | 3 | 400 |  |  |
| 3 (MG) | 56 | F | FCL, II | 3B | 0 | 0 | CD37 | 3 | 400 | 2 | Progression |
|  |  |  |  |  |  |  | CD19 | 3 | 400 |  |  |
| 4 (NW) | 62 | M | FCL, II | 4B | 4 | >2 | CD37 | 3 | 400 | 2 | MR$^a$ |
|  |  |  |  |  |  |  | CD19 | 3 |  |  |  |
| 5 (IS) | 63 | F | FCL, I$^b$ | 4B | 0 | >2 | CD37 | 3 | 500 | 2 | PR$^c$ |
|  |  |  |  |  |  |  | CD38 | 3 | 500 |  |  |
|  |  |  |  |  |  |  | CD37 | 3 | 700 | 1 | PR$^c$ |
|  |  |  |  |  |  |  | CD38 | 3 | 700 |  |  |
| 6 (RH) | 53 | M | CLL/SLL | 4B | 80 | >2 | CD37 | 3 | 900 | 2 | MR$^a$ |
|  |  |  |  |  |  |  | CD19 | 3 | 900 |  |  |

TABLE 2-continued

PATIENTS TREATED WITH FabFc₂ ANTIBODY

| Patient | Age | Sex | Diagnosis * | Stage | Neopl. cells in blood (10⁹/l) | Courses of chemo-therapy | FabFc2 Specif. | Doses | Total mg | Toxicity † | Outcome † |
|---|---|---|---|---|---|---|---|---|---|---|---|
| 7 (JK) | 51 | M | SLL | 4A | 18 | >2 | CD37 | 3 | 900 | 1 | Stable[a] |
|  |  |  |  |  |  |  | CD19 | 3 | 900 |  |  |
| 8 (JC) | 38 | M | MCL | 4B | 0.8 | >2[d] | CD37 | 3 | 800 | 1 | Stable[a] |
|  |  |  |  |  |  |  | CD19 | 3 | 800 |  |  |
| 9 (EV) | 55 | F | Burkitt-type | 1E | 0 | 0 | CD37 | 3 | 500 | 0 | CR[e] |
|  |  |  |  |  |  |  | CD38 | 3 | 500 |  |  |
| 10 (SS) | 28 | M | Mediasl large-cell | 3B | 0 | >2 | CD37 | 3 | 600 | 2 | PR[f] |
|  |  |  |  |  |  |  | CD38 | 2 | 400 |  |  |

Although the foregoing invention has been described in some detail by way of illustration and example for purposes of clarity of understanding, it will be obvious to one skilled in the art that certain changes and modifications may be practiced within the scope of the appended claims.

What is claimed is:

1. An intermediate having the general formula:

Fc—S—S—X wherein:

S—S is a disulphide bond;

X is a terminal group which is protonated at a relatively low pH of about 5 or less, such that said disulfide bond to X, S—S—X, is electrophilic and susceptible to reduction at a pH of about 5 or less, at which pH other disulphide bonds are resistant to reduction; and Fc is an Fc fragment, comprising four external sulphydryl groups, wherein said sulphydryl group on said Fc that is incorporated into said disulphide bond to X, S—S—X, is electrophilic and susceptible to reduction at a pH of about 5 or less, at which pH the three remaining external sulphydryl groups on said Fc are rendered by alkylation or incorporation into an interchain disulphide bond.

2. The intermediate of claim 1, wherein X comprises a primary amino group close to an S—S bond.

3. The intermediate of claim 1, wherein X is dithio-ethylamine or dithio-phenylamine.

4. The intermediate of claim 1, wherein X is a pyridyl compound.

5. The intermediate of claim 4, wherein said pyridyl compound is a 2-pyridyl or a 4-pyridyl derivative.

6. The intermediate of claim 5, wherein said 2-pyridyl derivative is derived from 2-,2'-dipyridyl disulphide and said 4-pyridyl derivative is derived from 4,4'-dipyridyl disulphide.

7. The intermediate of claim 1, in open hinged form, wherein three external sulphydryl groups on said Fc are alkylated.

8. The intermediate of claim 1, in closed-hinged form, wherein one external sulphydryl group on said Fc is alkylated, and two external sulphydryl groups are incorporated into an interchange disulfide bond.

9. The intermediate of claim 1, wherein said Fc is derived from human immunoglobulin.

10. The intermediate of claim 9, wherein said immunoglobulin is human gamma immunoglobulin, IgG.

11. The intermediate of claim 10, wherein said IgG is human IgG1.

12. The intermediate of claim 1, wherein said Fc is derived from monoclonal or polyclonal antibodies.

13. The intermediate of claim 1, wherein said pH is between about 3 to 5.

14. The intermediate of claim 13, wherein said pH is between about 4 to 4.5.

15. A process for the production of an open-hinge intermediate comprising:

(a) reducing two interchain disulphide bonds of an Fc fragment to form four external sulphydryl groups;

(b) reacting one external sulphydryl group of said Fc fragment of step (a) with a sacrificial group to form a first temporary species, Fc—S—S-Sacrificial group;

(c) rendering inert the three remaining external sulphydryl groups on said Fc fragment of said first temporary species by alkylation to form a second temporary species;

(d) reducing said second temporary species to remove said sacrificial group from said Fc fragment, thereby reforming one external sulphydryl group on said Fc fragment; and (e) reacting said reformed sulphydryl group of step (d) with a disulphide of the formula X—S—S—X to form said open-hinge intermediate Fc—S—S—X, wherein one sulphydryl group is incorporated into said disulphide bond to X, S—S—X, and three sulphydryl groups are alkylated, wherein said open hinge intermediate has the general formula:

Fc—S—S—X wherein:

S—S is a disulphide bond;

X is a group which is protonated at a pH of about 5 or less, such that said disulfide bond to X, S—S—X, is electrophilic and susceptible to reduction at a pH of about 5 or less, at which pH other disulphide bonds are resistant to reduction; and Fc is an Fc fragment that has been processed according to steps (a)–(e), comprising four external sulphydryl groups, wherein said sulphydryl group on said Fc that is incorporated into said disulphide bond to X, S—S—X, is electrophilic and susceptible to reduction at a pH of about 5 or less, at which pH the three remaining external sulphydryl groups on said Fc are inert due to alkylation.

16. A process for the production of a closed-hinge intermediate comprising:
  (a) reducing two interchain disulphide bonds of an Fc fragment to form four external sulphydryl groups;
  (b) reacting one external sulphydryl group of said Fc fragment of step (a) with a sacrificial group to form a first temporary species, Fc—S—S-Sacrificial group,
  (c) reacting said first temporary species with a disulphide of the formula X—S—S—X to form a second temporary species, wherein two external sulphydryl groups of said first temporary species are incorporated into an interchain disulphide bond and a third external sulphydryl group is electrophilic and susceptible to reduction at a pH of about 5 or less due to incorporation into a said disulphide bond to X, S—S—X;
  (d) reducing said disulphide bond to X, S—S—X, of step (c) at a pH of about 5 or less to reform one external sulphydryl group to form a third temporary species;
  (e) alkylating said one sulphydryl group of said third temporary species, thereby rendering it inert and forming a fourth temporary species;
  (f) reducing said fourth temporary species, to remove said sacrificial group from said Fc fragment and to reduce all interchain disulphide bonds, thereby reforming three external sulphydryl groups on said Fc fragment; and
  (g) reacting one of said reformed sulphydryl groups of step (f) with a disulphide of the formula X—S—S—X to form said closed-hinge intermediate Fc—S—S—X, wherein one sulphydryl group is incorporated into said disulphide bond to X, S—S—X, one sulphydryl group is alkylated, and two sulphydryl groups are incorporated into an interchain disulphide bond,
  wherein said closed-hinge intermediate has the general formula:

Fc—S—S—X wherein:
  S—S is a disulphide bond;
  X is a group which is protonated at a pH of about 5 or less, such that said disulfide bond to X, S—S—X, is electrophilic and susceptible to reduction at a pH of about 5 or less, at which pH other disulphide bonds are resistant to reduction; and
  Fc is an Fc fragment that has been processed according to steps (a)–(g), comprising four external sulphydryl groups, wherein said sulphydryl group on said Fc that is incorporated into said disulphide bond to X, S—S—X, is electrophilic and susceptible to reduction at a pH of about 5 or less, at which pH one external sulphydryl group on said Fc is inert due to alkylation and two are inert due to incorporation into an interchain disulphide bond.

17. A process for the production of an open hinge intermediate comprising:
  (a) reducing two interchain disulphide bonds of an Fc fragment to form four external sulphydryl groups;
  (b) alkylating three external sulphydryl groups on said Fc fragment of step (a) thereby forming a first temporary species, wherein three external sulphydryl groups are alkylated and one external sulphydryl group remains free; and
  (c) reacting said free external sulphydryl group of said first temporary species with a disulphide of the formula X—S—S—X to form said open hinge intermediate Fc—S—S—X, wherein one external sulphydryl group is incorporated into said disulphide bond to X, S—S—X, and three external sulphydryl groups are alkylated,
  wherein said open hinge intermediate has the general formula:

Fc—S—S—X wherein:
  S—S is a disulphide bond;
  X is a group which is protonated at a pH of about 5 or less, such that said disulfide bond to X, S—S—X, is electrophilic and susceptible to reduction at a pH of about 5 or less, at which pH other disulphide bonds are resistant to reduction; and
  Fc is an Fc fragment, comprising four external sulphydryl groups, wherein said sulphydryl group on said Fc that is incorporated into said disulphide bond to X, S—S—X, is electrophilic and susceptible to reduction at a pH of about 5 or less, at which pH three external sulphydryl groups on said Fc are inert due to alkylation.

18. A process for the production of a closed-hinge intermediate comprising:
  (a) reducing two interchain disulphide bonds of an Fc fragment to form four external sulphydryl groups;
  (b) alkylating one external sulphydryl group on said Fc fragment of step (a) thereby forming a first temporary species, wherein one external sulphydryl group is alkylated and three external sulphydryl groups remain free; and
  (c) reacting said first temporary species with a disulphide of the formula X—S—S—X to form said closed-hinge intermediate Fc—S—S—X, wherein one of said external sulphydryl groups is incorporated into said disulphide bond to X, S—S—X, two of said external sulphydryl groups are incorporated into an interchain disulphide bond, and one external sulphydryl group is alkylated,
  wherein said closed-hinge intermediate has the general formula:

Fc—S—S—X wherein:
  S—S is a disulphide bond;
  X is a group which is protonated at a pH of about 5 or less, such that said disulfide bond to X, S—S—X, is electrophilic and susceptible to reduction at a pH of about 5 or less, at which pH other disulphide bonds are resistant to reduction; and
  Fc is an Fc fragment, comprising four external sulphydryl groups, wherein said sulphydryl group on said Fc that is incorporated into said disulphide bond to X, S—S—X, is electrophilic and susceptible to reduction at a pH of about 5 or less, at which pH one external sulphydryl group on said Fc is inert due to alkylation and two external sulphydryl groups are inert due to incorporation into an interchain disulphide bond.

19. The process of claim 17, wherein said alkylating step (b) is carried out under conditions resulting in an average of 3.4 alkylations per Fc antibody fragment.

20. The process of claim 18, wherein said alkylating step (b) is carried out under conditions resulting in an average of 0.6 alkylations per Fc antibody fragment.

21. The process as in either claim 15 or claim 16, wherein said sacrificial group that is reacted with said Fc fragment in step 15(b) or 16(b) has one external sulphydryl group that is incorporated into a disulphide bond to X, Sacrificial group—S—S—X, and said sacrificial group is a member selected from the group comprising human serum albumin and Fab fragments derived from immunoglobulins selected such that said Fab fragment has a molecular weight greater than or equal to the molecular weight of said Fc fragment to which it is bound via said disulphide bond.

22. The process of claim 17, wherein said sacrificial group is an Fab fragment derived from a gamma immunoglobulin, IgG.

23. The process as in one of claims 15–19, wherein X comprises a primary amino group close to an S—S bond.

24. The process as in one of claims 15–19, wherein X is dithio-ethylamine or dithio-phenylamine.

25. The process as in one of claims 15–19, wherein said X is a pyridyl compound.

26. The process as in claim 25, wherein said pyridyl compound is a 2-pyridyl or a 4-pyridyl derivative.

27. The process as in claim 26, wherein said 2-pyridyl derivative is 2-,4'-dipyridyl disulphide and said 4-pyridyl derivative is 4,4'-diphyridyl disulphide.

28. The process as in one of claims 15–19, wherein said Fc antibody fragment is derived from human immunoglobulin.

29. The process as in claim 28, wherein said human immunoglobulin is human IgG.

30. The process of claim 29, wherein said human IgG is IgG1.

31. The process as in one of claims 15–19, wherein said Fc antibody fragment is derived from monoclonal or polyclonal antibodies.

32. The process as in either claim 15 or claim 16, wherein said sacrificial group is human serum albumin (HSA).

33. The process of claim 32, wherein said human serum albumin (HSA), is prepared by the following steps:
 (a) reducing said HSA to form a external sulphydryl group,
 (b) reacting said sulphydryl group of step (a) with maleimide to form $HSA(mal)_1$ possessing a maleimidyl group, and
 (c) reacting said $HSA(mal)_1$ of step (b) with dithiothreitol to form $HSA(SH)_1$ possessing a external SH group located at the end of an arm of about 15 Angstrom units long.

34. The process as in one of claims 15–19, wherein said alkylation is accomplished by using N-ethylmaleimide.

35. The process as in one of claims 15–19, wherein said pH is between about 3 to about 5.

36. The process as in one of claims 15–19, wherein said pH is between about 4 to about 4.5.

* * * * *